United States Patent
Zeller et al.

(10) Patent No.: US 11,596,923 B2
(45) Date of Patent: Mar. 7, 2023

(54) ALGAE THERMOPLASTIC COMPOSITION AND PROCESS OF MAKING

(71) Applicant: Algix, LLC, Meridian, MS (US)

(72) Inventors: Mark Ashton Zeller, Meridian, MS (US); Ryan Hunt, Meridian, MS (US)

(73) Assignee: Algix, LLC, Meridian, MS (US)

( * ) Notice: Subject to any disclaimer, the term of this patent is extended or adjusted under 35 U.S.C. 154(b) by 263 days.

(21) Appl. No.: 16/882,693

(22) Filed: May 25, 2020

(65) Prior Publication Data

US 2020/0384442 A1    Dec. 10, 2020

Related U.S. Application Data

(60) Provisional application No. 62/851,871, filed on May 23, 2019.

(51) Int. Cl.

| | | |
|---|---|---|
| *C09J 175/08* | (2006.01) |
| *B01J 20/26* | (2006.01) |
| *C12N 1/12* | (2006.01) |
| *C08G 18/72* | (2006.01) |
| *C08K 5/00* | (2006.01) |
| *C08G 18/08* | (2006.01) |

(52) U.S. Cl.
CPC ............ *B01J 20/267* (2013.01); *C08G 18/14* (2013.01); *C08G 18/72* (2013.01); *C08K 5/0016* (2013.01); *C12N 1/12* (2013.01); *B01J 2220/4843* (2013.01)

(58) Field of Classification Search
CPC ........ B01J 20/267; C08L 89/00; C08G 18/14; C08G 18/72

USPC ............................................ 523/102; 524/47
See application file for complete search history.

(56) References Cited

U.S. PATENT DOCUMENTS

| | | |
|---|---|---|
| 5,779,960 A | 7/1998 | Berlowitz-Tarrant |
| 8,524,811 B2 | 9/2013 | Shi |
| 9,375,703 B2 | 6/2016 | Harlin et al. |
| 2012/0007267 A1 | 1/2012 | Pawloski |
| 2017/0058451 A1 | 3/2017 | Smith et al. |
| 2017/0142978 A1 | 5/2017 | Falken |
| 2020/0283600 A1 * | 9/2020 | Shi .......................... C08J 3/226 |

OTHER PUBLICATIONS

International Search Report, dated Oct. 14, 2020 for PCT/US20/34461, 18 pages.

* cited by examiner

*Primary Examiner* — Terressa Boykin
(74) *Attorney, Agent, or Firm* — Loomis, Ewert, Parsley, Davis & Gotting, PC; Mikhail Murshak (57) ABSTRACT

An algae-based thermoplastic foam is provided having a protein-rich algae biomass selected from either microalgae, macroalgae or combinations thereof. The protein content is greater than or equal to 15% by weight of the algae biomass and the algae biomass is dried to a moister content of less than or equal to 15% by weight having an average particle size of up to 200 microns. The composition includes a resin configured to exhibit rheological properties suitable for blending with algae including a melting temperature less than 250° C. and a melt flow rate in excess of 0.01 g/10 min. The foam includes a foaming ingredient selected from the group consisting of crosslinkers, compatibilizers, plasticizers, accelerants, catalysts, blowing agents, other ingredients, and combinations thereof.

20 Claims, 1 Drawing Sheet

ALGAE THERMOPLASTIC COMPOSITION AND PROCESS OF MAKING

CROSS REFERENCE TO RELATED APPLICATION

This Application claims priority to and the benefit of U.S. Provisional Patent Application No. 62/851,871 titled "ALGAE THERMOPLASTIC COMPOSITION AND PROCESS OF MAKING," and filed on May 23, 2019, the disclosure of which is incorporated herein by reference in its entirety for all purposes.

TECHNICAL FIELD

The present disclosure relates generally to the field of an algae thermoplastic compositions and method of making the same.

DESCRIPTION OF RELATED ART

Thermoplastic compositions are often desired for consumer goods, particularly for footwear and other related industries. These thermoplastic compositions have applications in films, fibers, solid goods, and foams through processing techniques such as injection molding, blow molding, roto molding, cast film extrusion, blown film extrusion, bun foaming, injection foaming, compression foaming, profile extrusion, steam chest expansion foaming, autoclave foaming, and others. Foaming applications are especially interesting because of certain properties of these thermoplastic compositions.

The thermoplastic foam market, specifically flexible thermoplastic foams are widely used in markets with short lived products and made for consumers who are becoming increasingly eco-conscious. Therefore, demand exists for sustainable, biodegradable, and/or environmentally conscious product solutions.

Despite other attempts to solve the problems associated with forming an algae-based thermoplastic, none of these teach or suggest a material and/or method having the benefits and features of the present disclosure.

SUMMARY

The present disclosure provides for an algae-based thermoplastic compositions including an algae biomass and a resin. The algae biomass is selected from either microalgae, macroalgae or combinations thereof. The algae is protein-rich having a protein content of at least 15% by weight and dried to a moisture content of less than 15% by weight, having an average particle size of up to 200 microns. The dried algae biomass is at least 5% by weight of the thermoplastic composition. The composition includes a resin configured to exhibit rheological properties suitable for blending with algae including a melting temperature less than 250° C. and a melt flow rate in excess of 0.01 g/10 min. In an example, the algae biomass includes a dry weight of 15 to 90% protein, 5 to 50% carbohydrates, and 5 to 80% mineral and/or inorganic ash content.

For a foam composition, a foaming ingredient can be provided that is selected from the group consisting of crosslinkers, compatibilizers, plasticizers, accelerants, catalysts, blowing agents, other ingredients, and combinations thereof. The resin can be selected from the group consisting of polyesters, polyolefins, thermoplastic elastomers, styrenics, polyamides, polyethers, polyvinyl chlorides, thermoplastic polyurethanes (TPU), polybutylene adipate-co-terephthalate, polyethylene, and/or ethylene-vinyl acetate (EVA), and copolymers, and combinations thereof.

The present disclosure further provides for a method of forming an algae-based thermoplastic composition, the method includes: (a) grinding a protein-rich algae biomass forming an algae powder having at least 15% protein content by weight; (b) drying the algae powder to form a relatively dried algae biomass powder having a moisture content of less than 15% by weight; (c) premixing and preheating a thermoplastic resin to a desired temperature and viscosity to form a molten thermoplastic; (d) mixing the algae powder with the molten thermoplastic forming a thermoplastic-algae blend; (e) optionally adding any desired additives, plasticizers, compatibilizers and/or foaming agents; (f) dispersing the thermoplastic-algae blend from (d) or (e) (for example onto a roll mill stack); and (g) forming a predetermined final product or end product using the algae-thermoplastic blend. The final product or end-product functions and defines similar, better, and/or comparable characteristics to a final product or end product formed of the thermoplastic absent the algae.

For purposes of summarizing the disclosure, certain aspects, advantages, and novel features of the disclosure have been described herein. It is to be understood that not necessarily all such advantages may be achieved in accordance with any one embodiment of the disclosure. Thus, the disclosure may be embodied or carried out in a manner that achieves or optimizes one advantage or group of advantages as taught herein without necessarily achieving other advantages as may be taught or suggested herein. The features of the disclosure which are believed to be novel are particularly pointed out and distinctly claimed in the concluding portion of the specification. These and other features, aspects, and advantages of the present disclosure will become better understood with reference to the following drawings and detailed description.

BRIEF DESCRIPTION OF THE DRAWINGS

The FIGURES which accompany the written portion of this specification illustrate embodiments and method(s) of use for the present disclosure constructed and operative according to the teachings of the present disclosure.

The various embodiments of the present disclosure will hereinafter be described in conjunction with the appended drawings, wherein like designations denote like elements.

DETAILED DESCRIPTION

The present disclosure provides for algae-based thermoplastic compositions and methods of making such algae-based thermoplastic compositions. Moreover, these algae-based thermoplastic compositions have usefulness in foam-type applications. The algae-based thermoplastic compositions have been developed to produce commercially viable products including foams, fibers, films, injection molded articles, blown articles, cast parts, and other plastic articles consistent with a set of specifications set by industry. In some examples, the thermoplastic compositions improve foam product and end-product characteristics such as tear strength, adhesive bonding strength, biodegradability, elongation, and other properties. Foam products means a product composed at least partially of a polymer formed by trapping pockets of gas in liquid or solid. A foam end-product means a product or portion of a product that incorporates the produced foam. Examples of foam can include, but not limited to: thermoplastic elastomer, thermoplastic polyurethane (TPU), polybutylene adipate-co-terephthalate, polyethylene, and/or ethylene-vinyl acetate (EVA) foam. Examples of foam end-products include a cushion or a shoe component such as an insole, midsole or outsole.

Co-owned and pending patent application Ser. No. 15/261,767 filed Sep. 9, 2016 titled "ALGAE-DERIVED FLEXIBLE FOAM, AND A METHOD OF MANUFACTURING THE SAME"; Ser. No. 15/356,213 filed Nov. 18, 2016 titled "ALGAE-DERIVED FLEXIBLE FOAM, AND A METHOD OF MANUFACTURING THE SAME"; and Ser. No. 16/396,370 filed Apr. 26, 2019 titled "ELASTOMER COMPOSITE INCLUDING ALGAE BIOMASS FILLER" describe various embodiments of algae-based polymer compositions and materials and are hereby incorporated by reference in their entirety.

Figure 1:
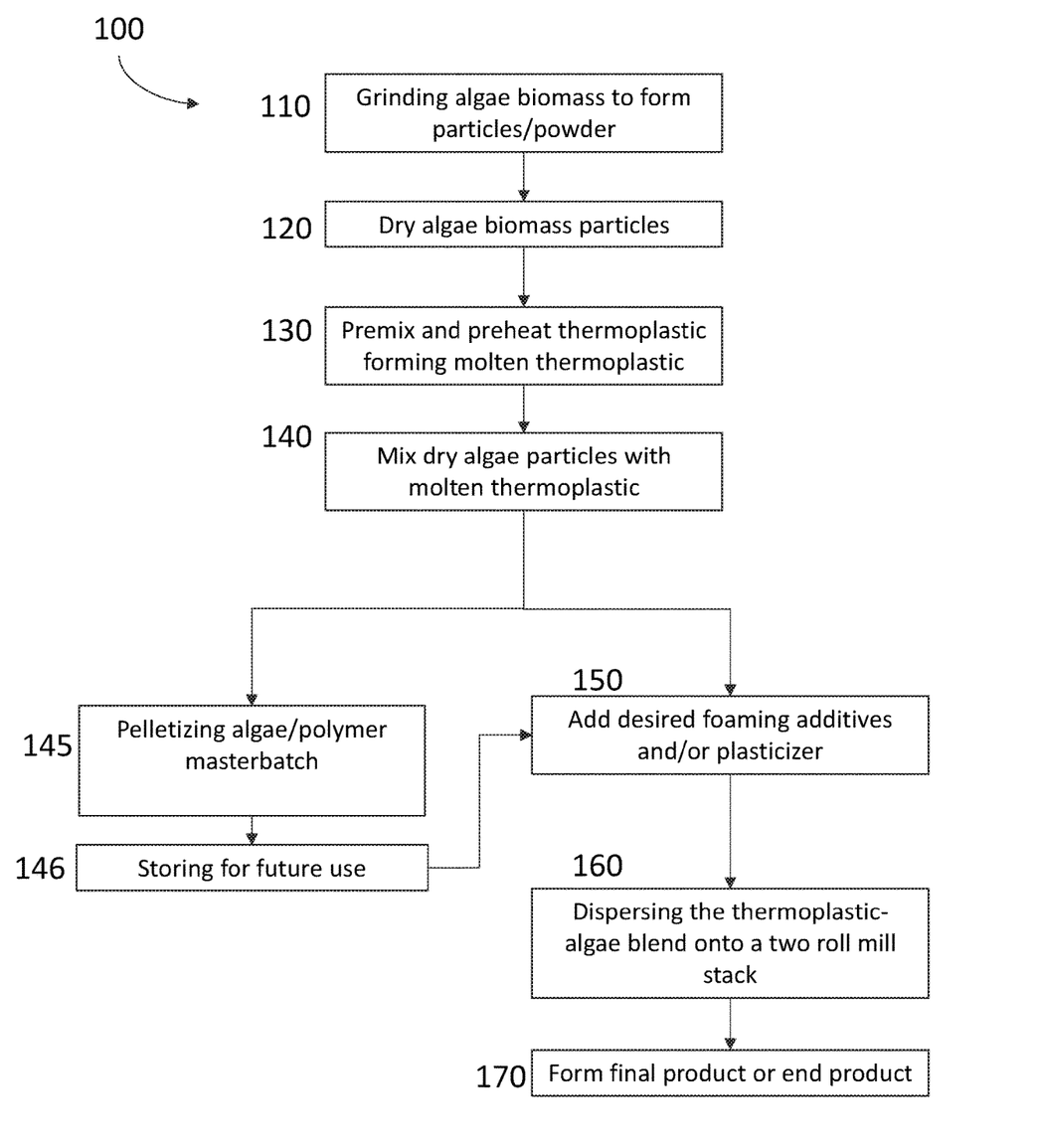
FIG. 1 is flow chart of a method of forming a thermoplastic-algae composition according to the present disclosure.

Referring to the process of FIG. 1, a flowchart illustrating a process for forming an exemplary algae-based thermoplastic is shown. Process 100 starts with step 110 which includes grinding an algae biomass. This can include forming an algae powder having an average diameter particle size of up to 200 microns. From there the process moves to step 120 where the algae biomass is dried forming a dried or relatively dried algae biomass powder. The dried algae biomass should have a moisture content of 15% or less. The process continues to step 130 where the thermoplastic resin is premixed and preheated to a desired temperature and viscosity forming a molten thermoplastic. In an example, the resin is premixed and preheated to a temperature in a range of (90° C.-250° C.) for (1 to 30 minutes) to achieve a polymer viscosity sufficient to accept a particulate filler where in the melt flow rate of the polymer is in excess of 0.01 g/10 min. The process continues to step 140 where the algae biomass from step 120 is mixed with molten thermoplastic from step 130. The process may continue with step 140 producing a highly loaded algae thermoplastic masterbatch which may be pelletized in step 145 to form algae blended thermoplastic pellets. The algae blended thermoplastic pellets of step 145 may be further stored in step 146 for an indeterminate period before it is further used in a foaming or other plastic process. At step 150, any desired additives, plasticizers, compatibilizers and/or foaming agents are added to the mixture of step 140 forming a thermoplastic-algae-blend designed for foaming. The thermoplastic-algae-blend is then dispersed in step 160. In this example, the dispersing is performed onto a roll mill stack, but may also occur in a twin screw extruder along with steps 130, 140, and 150, wherein the twin screw extruder accomplishes all of these steps in a continuous process as opposed to the batch process exemplified here. In step 170, a final product is formed using the algae-thermoplastic blend dispersed from step 160. In an example, the final product should function and have similar, better, and/or comparable characteristics to a final product formed of a thermoplastic product formed absent the algae content. Examples of these characteristics include mechanical, physical, rheological, degradability, or other properties of the material.

The present disclosure provides for an algae-based thermoplastic composition formed by a combination of a protein-rich algae biomass, and a resin. Protein-rich algae biomass means a biomass having at least 15% protein content by weight. In an example, a thermoplastic foam can be formed by using a foaming ingredient with the algae biomass and the resin. In one form, the algae biomass can be provided in its raw form as it is found, obtained, or produced in nature. This can include a biomass formed of microalgae, macroalgae, both microalgae and macroalgae, and/or components or byproducts of these algae materials. The algae biomass can also be provided as an extract from microalgae or macroalgae such as seaweed.

In an example, algae biomass which contains greater than 15% protein content by weight including greater than 20%, greater than 25% protein content and greater than 30% protein content can be desirable for thermoplastic compositions. Protein content has shown to have thermoplastic characteristics making it more than just a filler including but not limited to a viscoelastic modulus, the ability to take on the rheological characteristics and flow align to a melt, the ability to change shape under temperature and pressure, and other characteristics. These characteristics are not exhibited by the carbohydrates or mineral content found in algae which behave as fillers only. In addition, to extracting to achieve a desired composition, a less energy intensive and more economical alternative to existing processes, includes using multiple algae sources wherein each algae source used has naturally high levels of a targeted compound and blending them to achieve a biomass composition with desired qualities.

In an example, diatoms, coccalithophores, coralline and other algae sources high in mineral content may be used to form a desired thermoplastic composition wherein higher mineral contents are desired such as when a higher loading by weight is desired since the density of the mineral allows for a greater inclusion rate in a polymer before polymer/filler phase interactions begin to break down.

Blue green algae, also known as cyanobacteria and microalgae or single cellular algae especially from the phylum chlorophyta, tend to be naturally high in protein especially when collected from nutrient rich environments such as might exist when collected from environmental remediation efforts, wastewater treatment, or as a post extracted meal from biofuels extraction. Common types of algae found naturally include chlorella, scenedesmus, spirulina, chlamydomonas, chlorococcum, phormidium, oscillatoria, spirogyra, chroococcus, dunaliella, prasiola, nostoc, and vaucheria. High protein content is desirable in many applications because it behaves like a thermoplastic, when combined with the resin, and therefore, processes more effectively in processes that have rheological constraints and contributes its own polymeric characteristics to the bulk properties of the material. In addition, algae high in protein has higher levels of bioavailable nitrogen and phosphorus which when used with biodegradable polymers greatly enhances the rate and circumstances in which biodegradation will occur making the product better suited for biodegradation in environments it otherwise may not have been usable. Typically found commercially, biodegradable polymers are unfilled or filled with starch, which lack these nutritive characteristics leading to slower biodegradation and no plant growth stimulation. However, this can be troubling for composting environments. The industrial composting environments for which these products are designed, suffer from their introduction since they only provide sources of carbon, which composters have in abundance, and composters need to maintain an adequate ratio of Carbon to Nitrogen to achieve fast biodegradation. The desired ratio is typically 25 to 30 grams of Carbon per gram of Nitrogen. Excess carbon produces slow composting and lower quality compost that facilities are not able to sell as easily. Excess nitrogen produces to fast of a biodegradation rate and leads to stinky compost from the growth of less desirable microorganisms that do not compete as well as under the proper carbon to nitrogen ratio conditions.

In an example, the present disclosure provides for a product having a polymer with 20% algae by weight with a protein-rich content around 40%. Using a standard protein to nitrogen conversion factor of 6.25, means the product would contain about 1.25% nitrogen by weight obtaining an 80 to 1 carbon to nitrogen ratio which is about 3 times the desired ratio. However, this is a significant improvement over traditional biodegradable resins available which typically have a carbon to nitrogen ratio in excess of 300 to 1 of carbon to nitrogen. This reduces the demands on industrial composters to find food waste and animal manures which are rich in nitrogen to offset the lack of nitrogen in biodegradable polymers. For instance, studies have shown that a ratio of about 42 parts nitrogen rich compost from food or animal waste to 1-part traditional polymer are necessary to achieve a proper carbon to nitrogen ratio in compost. In contrast the protein-rich algae compositions disclosed herein would need about 4 parts of nitrogen rich material to every 1 part of protein-rich algae biodegradable composite. Therefore, about 10 times as much biodegradable material can be composted for the available animal and food waste used by composting facilities without slowing down productivity of the facility when using the composition disclosed herein. Other protein-rich sources from animals or plants are not commercially available because they are either very expensive to produce or in most cases directly compete with food production, but the algae described herein is widely abundant in adequate protein content ranges and does not interfere with food production and in many cases its removal improves food production. Therefore, algae compositions as described herein are uniquely well suited to provide these benefits to biodegradable materials.

Macroalgae, such as seaweeds, tend to be high in carbohydrates including structural carbohydrates and food storage carbohydrates such as starch. Carbohydrates, unless chemically modified, do not tend to behave like a polymer. Typically, they are thermally sensitive and tend to burn undergoing Maillard and caramelization reactions. Carbohydrates also generate lower filler loadings by weight compared to mineralized biomass sources because they are less dense. Therefore, increased carbohydrate content tends to be the less desirable unless significant extraction work and or chemical modification work is conducted such as hydroxypropylation of the carbohydrates to improve their intermolecular interactions. However, fibers can be obtained from algae rich in carbohydrates which can be used as reinforcing fillers with anisotropic characteristics. These can be helpful in scenarios in which achieving a maximized toughness or strength in one direction is desired, for example, with respect to fiber, coating, or film manufacturing.

Protein-rich algae biomass can be sourced from marine, brackish, and/or freshwater algae sources including those from the following families of algae: Cyanophyta, Charophyta, Chlorophyta, Phaeophyta, Chrysophyta, Bacillariophyta, Haptophyta, and Rhodophyta. Microalgae or unicellular algae sources can be used because these species grow relatively fast, are naturally high in protein, are effective at removing water-borne and air-borne pollutants and are considered a nuisance in many bodies of water. In some circumstances these microalgae may even form blooms which are larger than normal concentrations of these organisms proliferating in a particular area, which can have destructive effects on the ecosystem and local economies. Therefore, it can be helpful to remove these microalgae from ecosystems with an overabundance of nutrients to prevent or mitigate the damage from blooms. The nutrient rich conditions, where these destructive blooms of microalgae are typically found, can include the fastest growing and most protein-rich algal species. These species of algae can exhibit beneficial thermoplastic characteristics due to protein contents natural tendency to denature under elevated heat and/or pressure. This denaturation quality of proteins allows them in typical plastic processing environments to lose their initial form and conform to the optimal form driven by the processing of the thermoplastic melt. This allows these protein-rich algae compositions to outperform most other algae types in most thermoplastic applications because they process more easily and reduce the overall internal stress in the finished part since they conform to the desired finished parts shape in their denatured state more readily. This is especially important in flexible thermoplastic applications where the structural rigidity of carbohydrate rich or ash rich algae biomass works against the desired properties of the finished parts.

In yet another embodiment, macroalgae may be used. In one example, the macroalgae is used when an extracted meal from macroalgae is formed, which eliminates or reduces the concentration of structural and food storage carbohydrates naturally produced in these species.

In yet another example of the present disclosure, the composition of algae biomass includes a dry weight of 15 to 90% protein including 20 to 85%, 25 to 80% as well as 30 to 75%, 5 to 50% carbohydrates by weight including 10 to 45% as well as 15 to 40%, and 5 to 80% mineral or inorganic ash content by weight including 10 to 75% as well as 15 to 70%. In another example, the algae biomass includes a dry weight of 35-50% protein, 5-30% carbohydrate and 25-40% ash and sourced from algae grown from a waste water facility in a controlled environment. In an even further example, the algae biomass includes dry weight of 41% protein, 26% carbohydrate and 33% ash and sourced from wild grown algae.

In yet a further example, the moisture content of the algae is less than 15% by weight including less than 10% as well as less than 5%. Increasing moisture content increases the insulation of the material from overheating and forming agglomerates while blending into the thermoplastic. However, for manufacturing, it also increases demands on venting and screw design to handle the elevated moisture content and steam formed. Moisture contents of less than 0.5% including less than 1% as well as less than 2% and 3% are less desirable in the algae since they significantly increase the risks for burning the algae before it is incorporated.

In another form, the algae is milled to an average particle size with a d99 less than about 200 micron including a d99 less than about 140 microns as well as a d99 less than about 80 microns and further less than 50 microns. Further the average particle size used should include about 1 to 80 micron including 5 to 70 micron as well as 10 to 60 micron. Larger particle sizes should be selected in some cases since smaller particle size may increase the risk of agglomerate formation. However, especially in the case of thin films and fibers, small particles may be needed because protein-rich biomass only has some ability to change its shape in a melt flow. These smaller particles will allow the biomass to pass through screen packs and/or reach a target size of the fiber or films.

In addition to tailoring the characteristics of an end product by changing the composition of the algae biomass the addition and selection of a compatibilizer can change a resulting characteristic of a thermoplastic composition. A compatibilizer is not always required and is understood to confer benefits only under certain circumstances. This is especially true in the case of protein-rich compositions since they do not necessarily act only as fillers and the addition of compatibilizers can tend to cause the algae biomass to act more as a filler in the polymer matrix and eliminates the polymeric characteristics of the material.

Compatibilizers can be used to facilitate and enhance polymerization and combining of algae biomass to the resin when forming a desired composite material. Compatibilizers have been shown to be effective when toughening or strength enhancing characteristics of the desired material or composition are desired. In some circumstances, elongation, Din Abrasion and other characteristics of the material can be compromised with the presence and use of a compatibilizer. Compatibilizers can be selected from any class of commercially available compatibilizer. Common compatibilizers include those having glycidyl methacrylate, butyl acrylate and maleic anhydride functionalization. Compatibilizers with this type of functionalization tend to be block copolymers or a grafted compatibilizer, but reactive compatibilizers or coupling agents may also be used. These include but are not limited to coupling agents such as peroxides, isocyanates, glyoxal and other known coupling agents. Other processing aids such as rheology modifiers, surfactants, plasticizers, dispersing aids, antioxidants, flame retardants, moisture scavengers and others may be added, but are not always required. In prior examples, using these aids especially in the case of plasticizers was thought to be effective, but in the present disclosure, plasticizers are rarely necessary and often may lead to the formation of more agglomerates in the algae biomass due to a slower incorporation of the biomass caused by lubrication of the polymer melt and an increase of the polymer melts viscosity due to poor shear heating. Plasticizer use is rare in commercially applications, but in conditions when very high algae contents are desirable, plasticizers may provide a considerable benefit. Processing aid use and selection will depend on the product properties desired as well as a need to address processing hurdles, which arise when working with a thermoplastic composition. In yet another example, the composition is formed in the absence of a plasticizer.

The base resins suitable for use with algae to form a desired thermoplastic composition include a broad range of resins including but not limited to synthetic, plant-based, bio-based, renewably-sourced, petroleum-sourced resins and combinations thereof. In an example, the resins include: polyesters such as polyethylene terephthalate (PET), polybutylene terephthalate (PBT), polyethylene terephthalate glycol (PETG), polytrimethylene terephthalate (PTT), polycarbonate, and others, biodegradable resins such as polylactic acid (PLA), polybutylene succinate (PBS), polybutylene adipate-co-terephthalate (PBAT), polyhydroxyalkanoates (PHA) and others, polyolefins such as polyethylene (PE), polypropylene (PP), polybutene (PB), polyisobutylene (PIB), and others, thermoplastic elastomers such as thermoplastic polyurethanes (TPU), ethylene vinyl acetate (EVA), thermoplastic polyolefin elastomers (TPO), thermoplastic vulcanizates (TPV), thermoplastic copolyesters (TPE-E), thermoplastic polyamides (TPA), Thermoplastic styrenic block copolymers (TPS), Thermoplastic ester-ether copolymers (TPC), Thermoplastic amide-ether copolymers (TPE-A), and others, Styrenic resins such as polyacrylonitrile butadiene styrene (ABS), polyacrylonitrile styrene acrylate (ASA), polystyrene acrylonitrile (SAN), Polystyrene butadiene (SB), polystyrene (PS) and others, polyamides such as nylon and it's derivatives and vinyl containing thermoplastics such as polyvinyl chloride (PVC), polyvinyl alcohol (PVA), polyvinylidene chloride (PVDC) and others.

While these base resins are suitable for incorporation with algae biomass, certain characteristics of a resin will make it a more suitable candidate for processing with algae. For instance, resins with a higher melt flow index allow the algae to incorporate in sooner as well as with lower shear heat of the algae and will produce a masterbatch with better properties for processing in an end product manufacturing in many cases so long as sufficient melt strength is maintained. Algae which is rich in protein and low in carbohydrates has been demonstrated as being suitable for processing at up to 250° C. without burning when shear is controlled and without the addition of processing aids to reduce burning so base resins with melting points below 250° C. including below 240° C., below 220° C. as well as below 200° C. are desired, especially when no additional processing aids to address burning are being used such as antioxidants or shear reducing additives such as lubricants, plasticizers, or rheological modifiers. Further resins with elevated processing temperatures can increase the likelihood of cooking the material and generating odors comparable to cooked plant proteins and/or fishy malodors. Higher viscosity polymers are more likely to require processing aids so the lowest viscosity polymer which has a molecular weight suitable to achieve desired end product properties and which has enough melt strength to be processed without excessive failures in part production. Polymers with excessively high viscosity are likely to exhibit a melt flow rate lower than 0.01 g/10 min including 0.1 g/10 min as well as 0.5 g/10 min and 1 g/10 min when measured at 190° C. with a 2.16 kg test weight. Base resin selection should further consider the intended properties of the end product and be tailored to match a targeted material's properties as desired.

Thermoplastic compositions comprising algae are useful in a number of markets, however foam-related markets present unique advantages. Foams are generally higher value commodities, which have higher pricing and customers which are interested in telling sustainable manufacturing stories. These markets include, among others, automotive, footwear, apparel, consumer goods, sporting goods and other customers. Foams also go through an off-gassing period, which is standard in foam manufacturing and allows excess gas to be expelled as the foam reaches its final shape. This allows any odor generated during processing to be largely removed all at once. In addition, foams typically use lower melting point resins such that they will go from molten to solid slow enough for internal stresses in the foam to be relieved and a better foam to be produced. As such, foams as a target for algae blended thermoplastic compositions are desirable and described in detail individually.

In an example, an algae-based foam composition is formed by a combination of algae biomass, a foaming ingredient, and a resin. The algae biomass can be provided in its raw form as it is found, obtained, or produced in nature. This can include a biomass formed of microalgae, macroalgae, both microalgae and macroalgae, and/or components or byproducts of these algae materials. In an example, the algae biomass is protein-rich algae biomass. The algae biomass can also be provided as an extract from microalgae or macroalgae such as seaweed.

The foaming ingredient or ingredients are provided to trigger or produce a foam when combined with the biomass and the resin. This can include a catalyst and/or a compatibilizer operable to facilitate combining the algae biomass with the resin. In an example, the resin and the foaming ingredient are sufficient to produce a thermoplastic.

The resin can include thermoplastic resins which are sufficient for foaming. Examples include but are not limited to synthetic, plant-based, bio-based, renewably-sourced, petroleum sourced resins and combinations thereof. The resins further are resins suitable for use with algae as described previously.

In an example, algae biomass contains a dry weight fraction of protein of at least 15% and up to about 90% In another example, the dry weight fraction of protein can be found in a range from about 25% to about 80%, and in yet a further example the range is from about 30% to about 70%. These ranges can be modified and include variations of protein weight fraction from about 20% to about 80%, about 20% to about 70%, or from about 25% to about 90%, from about 25% to about 70%, and from about 30% to about 90%, and from about 30% to about 80%.

The protein fraction of the algae biomass composition can contribute many of the desirable characteristics achieved in the resulting foam and foam end products. Proteins react to heat and pressure by denaturing and unfolding to form moldable polymers, which can then take on a targeted shape for an end product. This plastic-like characteristic in the heated or molten state of a composite allows for better foam properties with less of the negative characteristics associated with using fillers in foams. Additionally, the proteins contain function in both hydrophilic and hydrophobic regions allowing some compatibility with most polymer systems which tend to be largely hydrophobic. However, in some embodiments, proteins in the presence of small molecule carbohydrates such as mono- and di-saccharides can crosslink to each other in Maillard reactions and form small accumulations of proteinaceous material called agglomerates which can harm the foam properties.

In an example, the dry weight carbohydrate fraction of the algae biomass composition is about 50% or less. In another example, the dry weight of the algae biomass composition is fraction is 40% or less. In some examples, the dry weight of the algae biomass composition is fraction is 30% or less. The carbohydrate fractions generally include structural and food storage types. The structural carbohydrates can be selected from the group consisting of: cellulose, hemicellulose, pectin, lignin, chitin, carrageenan, suberin, cutin, agar, peptidoglycans, and others and combinations or variations thereof. These structural carbohydrates under heat and pressure typically do not change shape and as such, serve as structural reinforcing agents with little or no plastic like characteristics. This can contribute to desired features and characteristics of the final foam product or foam end products.

The moieties found in carbohydrates can often inhibit, interfere, and/or interact with crosslinkers, foaming gas diffusion, cell expansion and size, and other important aspects of foam formation. Food storage carbohydrates can also be found in algae, including but not limited to alginate, starches like amylose amylopectin, and others. In addition to the problems found in structural carbohydrates, food storage carbohydrates are more temperature sensitive and readily degrade, in the presence of moisture, to saccharides which can produce caramelization, Maillard, and other side reactions, burn readily, and yield other consequences which are destructive to foam properties.

A modified carbohydrate fraction may be of interest in foaming such as trans-esterification or other modification of the carbohydrates which would change their moieties and chemical behavior. Such modifications may eliminate many of the negative side effects of carbohydrates, but these modifications may also substantially increase the cost of the biomass and make it less economical than simply selecting compositions which have desired characteristics already.

If rigid foam compositions with significant structural reinforcements are desired, increasing mineral contributions from algae in biomass can be effective. In some examples, increasing mineral content is preferred as compared to increasing the carbohydrate weight fraction. Algae types, including but not limited to diatoms, coralline algae, coccolithophore, as well as others have been shown to mineralize a significant portion of their biomass and can be used to increase the targeted properties of a material as a functional filler. Traditional mineral fillers are also available on the market from mining and other sources, but these sources have a less favorable environmental impact. The use of algae biomass with significant mineralization may be beneficial. Additionally, using algae derived minerals may provide added technical benefits due to the larger surface area, which can impact nucleation and other foaming processes to yield more uniform cell size distributions, greater cell density, and other improvements to foam properties. Minerals are also known to be inert in the heat, pressure, and reactions during foaming, thus making them desirable candidates as structural reinforcing aids.

In a further embodiment, the algae biomass composition includes minerals having a dry weight ash fraction in concentrations from about 5-85%. In another example, the concentration of minerals in the algae biomass composition is between about 10-75%, and in yet another example, the fraction is between about 15-65%. The mineral fraction is a relatively dominate portion of the biomass fraction which is not protein. These ranges can be modified and include variations of mineral dry weight ash fraction from about 10% to about 70%, about 10% to about 60%, or from about 15% to about 80%, from about 15% to about 60%, and from about 20% to about 80%, and from about 20% to about 70%. The dry weight ash fraction will generally include the beneficial mineralized biomass as well as some salts and other inorganic fractions. The salt and other inorganic fractions can be reduced if desired by washing biomass before drying if necessary.

In yet another embodiment, an algae-based foam product further includes a foaming ingredient that is provided to produce the foam. The foaming ingredient may include but is not limited to crosslinkers, compatibilizers, plasticizers, accelerants, catalysts, blowing agents, other ingredients, and combinations thereof. Crosslinkers may include but are not limited to peroxide based, isocyanate based, sulfur based, aziridine based, dialdehyde based, and other crosslinking agents based on the specific polymer systems requirements. For example, dicumyl peroxide may be used with Ethylene-vinyl acetate (EVA) or Polyethylene (PE); isocyanate may be used to link polymers with hydroxyl or amine moieties as well as proteins into the foam matrix; sulfur-based crosslinking may be used in SBS polymer systems; glyoxal may be used to crosslink algae and EVA, among other examples. These crosslinkers generally act to change the kinetics of gas flow exiting the polymer matrix to balance cell formation against gas escape and may also be used to help compatibilize algae to the polymer matrix.

Compatibilizers are operable to aid the algae in interacting with the polymer matrix and reduce phase separation. Since phase separation is a principal cause of agglomerate formation, compatibilizers can be effective in developing foam compositions which exhibit the benefits of algae-based compositions without suffering undesired consequences. Compatibilizers, include but are not limited to, side chain modified and grafted polymers, block co-polymers, crosslinkers targeting the algae, wetting agents, other compatibility aids, and combinations thereof.

Plasticizers allow for the reduction of shear which can create thermal spikes during mixing and lead to agglomerate formation, gel formation, and many other negative conditions in a foam. The necessity of plasticizers is dependent on the mixing process used to make a foam.

Accelerants and catalysts promote a faster reaction of foaming gas release or crosslinking depending on where they are targeted. Accelerants and catalysts take many forms based on the targeted crosslinker or blowing agent. Any agent which works to speed up the action of a crosslinker or blowing agent or which allows the action of a crosslinker or blowing agent to occur in conditions it otherwise would not act would be considered an accelerant or catalyst, respectively. Accelerants and catalysts can be used in circumstances in which there is an economic benefit to faster part manufacturing or the use of less energy. Accelerants and catalysts may also be used to reduce the required temperature of reaction to prevent the cooking of algae and the generation of foul odors or to balance the rate of gas generation and crosslinking reactions to improve foam cell formation and bubble growth.

Blowing agents are the constituents of a foam which produce a gas and generate cell formation, proliferation, and/or growth. Blowing agents may be chemical or physical blowing agents. Chemical blowing agents produce a gas through a decomposition reaction breaking a molecule down into its constituent gases. Physical blowing agents are molecules which at a certain temperature and pressure will become a gas, but exist as a liquid or solid at the operating conditions experienced prior to foaming. Blowing-gas type selection and quantity are determined on the basis of desired manufacturing environment, expansion ratio, mold characteristics, the thermoplastic polymer being used and corresponding gas saturation properties for that polymer, and/or gas yield.

Thermoplastic resins come in various chemical classes such as polyesters, polyolefins, thermoplastic elastomers, styrenics, polyamides, polyethers, polyvinyl chlorides, polyurethanes, and copolymer combination thereof. The thermoplastic resins can include, but not limited to, a polymer selected from the group consisting of ethylene vinyl acetate (EVA), polyvinyl chloride (PVC), polyethylene (PE), polypropylene (PP), polystyrene (PS), polyolefin elastomers (TPO), thermoplastic polyurethane (TPU), styrene butadiene styrene and styrene ethylene butylene styrene (TPR), polylactic acid (PLA), polybutylene adipate-co-terephthalate (PBAT), polybutylene succinate (PBS), polyethylene terephthalate (PET), nylon in its various forms (PA), polybutylene terephthalate (PBT), others, and combinations thereof. These thermoplastics can determine expected bulk mechanical properties of a finished foam and foam end product and establish many other aspects of a final foam composition. In an example, criteria used in thermoplastic selection includes avoiding high melting points, which can lead to cooking of the algae and foul odor generation. In an example, sufficient melting point temperatures less than 250° C. are desired including temperatures less than 230° C., as well as less than 210° C. as well as temperatures less than 190° C. In a further example, the resin of the thermoplastic should have a melt flow rate in excess of 0.01 g/10 min.

The present disclosure provides for a foam composition including algae, a thermoplastic, and a foaming ingredient sufficient to make an algae-based foam. The ingredients may be processed in a number of ways to generate the algae-based foam. In an example, algae is processed in order to be suitable for inclusion into the thermoplastic with a low risk of agglomeration. In one form, if extraction is required to achieve an algae composition which is suitable, then the extraction should be done first. A sufficient moisture content for the algae can be less than about 15% moisture by weight including less than about 10% moisture by weight as well as less than about 5% moisture by weight. Moisture contents of less than 1% including less than 2% as well as less than 3% are not desired in the algae since they significantly increase the risks for burning the algae before it is incorporated. In another form, the algae is milled to a particle size with a d99 less than about 200 micron including a d99 less than about 140 microns as well as a d99 less than about 80 microns. Further the average particle size used should include about 1 to 80 micron including 20 to 70 micron as well as 30 to 60 micron.

Extracted protein meal from algae is in some cases a byproduct of other product manufacturing processes. For instance, alginate, agar, nutraceuticals, biofuels and other products are extracted from algae leaving behind protein-rich meal. This protein-rich meal may be used as-is or in some cases may be washed or further extracted to produce meal with higher protein content, which is free of saccharides, or to remove other value-added co-products. In some cases, extraction may improve the properties of the resulting algae-based foam products and may lower cost through the fractionation and valorization of useful co-products.

Drying algae can be conducted through both mechanical and thermal means. In an example, raw microalgae biomass or extracted algae meal can be obtained as either a slurry at 0.5 to 15% by weight solids or it may be available as a wet cake or paste at 15-30% solids. This can then be dried to above 85% solids including greater than 90% solids as well as greater than 95% solids in order to effectively incorporate the algae into a thermoplastic. In some examples, drying before the algae is milled is effective to improve the economics, efficiency, and throughput of milling. However, in some cases milling is done on wet materials and drying needs to be conducted on wet materials such as in wet media mills like ball mills. Mechanical drying or dewatering can be done to reduce the risks of burning and generating foul odors in addition to improving the economics of drying. Examples include but are not limited to techniques such as belt filter pressing, centrifuge dewatering, screw pressing, plate and frame pressing, and others. Assisted thermal drying may also be done and is often effective in situations including, but not limited to, microwave drying, drum drying, heated screw drying, hot air convective drying, spray drying, and others. Passive thermal drying such as solar drying can also be used in some cases but increases the risk of foul odor generation due to biomass degradation if solar drying leads to prolonged periods of algae biomass storage before it is sufficiently dried. Additional directed electromagnetic wave or sound wave technology can be used to rupture a cell before or during drying to improve water removal. A sufficient moisture content for the algae can be less than about 15% moisture by weight including less than about 10% moisture by weight as well as less than about 5% moisture by weight. Moisture contents of less than 0.1% including less than 1% as well as less than 3% are not desired in the algae since they significantly increase the risks for burning the algae before it is incorporated.

Milling algae is typically done in dry mills but in some cases wet milling may be desired. Dry milling processes include jet mills, hammer mills, media mills, air classifying mills, grinding mills, and others. Algae's friability tends to be related to its moisture content when milled so effective drying often means more effective milling. Algae can be classified during milling or can be sieved after milling to obtain the particle size targeted for the desired algae-based plastic compositions. In the case of foams, in an example, a particle size with a d99 less than 200 microns including less than 140 microns as well as less than 80 microns can be targeted. The particle size can be reduced to the point that the algae can be readily dispersed in the polymer matrix and will not increase cell size or change cell shape when foaming, but unless counteracted through other actions, too fine a particle size can lead to an increased risk of agglomerate formation.

Once the algae have been milled and dried, they are ready to be incorporated into the thermoplastic composition along with the foaming ingredients sufficient to make an algae-based foam. Mixing the algae with the thermoplastic and foaming ingredients can be done with conventional mixing equipment used in the plastics industry. For example, it can be blended with a Banbury mixer and two mill roll stacks or via an extruder such as a twin-screw extruder. Other mixing techniques may be used but are not elaborated in this disclosure. Shear reduction can be a driving concern to prevent agglomerate formation. In either case the algae is best added to molten or semi-molten thermoplastic to reduce the shear it experiences while mixing. In the case of Banbury mixers, this means the thermoplastic should be added before the algae and sufficiently mixed and/or plasticized to allow it to readily accept and disperse the algae before it is added.

In an example, after all of the remaining foaming ingredients sufficient to form a foam have been added in the Banbury mixer, the finished composition can be further mixed and distributed on a two mill roll stack by using folding and layering techniques to achieve an even distribution. When using the two mill roll stack the composition should be kept at an elevated temp which does not begin crosslinking or begin to set off foaming, but reduces the viscosity of the composition as much as possible. This will help to reduce high shear and prevent agglomerate formation. Additionally, the gap between rollers can be adjusted to a wider gap distance and more passes through the two mill roll stack can be used to further reduce the risk of high shear and agglomeration. After the two mill roll stack step, the composition should have the algae sufficiently dispersed therein and distributed in order to foam and can be further worked and foamed to achieve a desired foam product.

In a further example, the algae is mixed via extruder, like a twin-screw corotating extruder. The twin-screw extruder offers flexibility in mixing conditions allowing the user to control shear and prevent agglomerate formation and it is a continuous process making the algae composition production more efficient and reducing cost. When mixed in a twin-screw extruder, the thermoplastic and other non-shear sensitive ingredients should be added in the feed throat and should be mixed in a back section of the extruder with high shear mixers and high heat to produce a consistent and low viscosity melt flow quickly. The algae, along with other shear sensitive ingredients, should then be added downstream via side feeders or comparable feeding equipment at which point barrel temperature can be lowered and low shear distributive mixing elements can be used. Similar techniques can be applied with single screw or counterrotating twin screw extruders, however they are more limited in terms of shear reduction and flexibility of screw design. Since extruders generally produce pellets the final composition can readily be used in most types of foaming equipment without problems.

The protein-rich algae compositions described herein, when foamed demonstrate novel properties which are beneficial in some situations. Benefits of the algae-based foam compositions detailed herein include enhanced surface polarity, tailorable material property benefits, carbon sequestration and carbon credit generation, and other environmental benefits. The protein-rich algae compositions described herein when foamed demonstrate novel properties which are beneficial. Enhanced surface polarity provides a benefit in water borne adhesive bonding and bond strength which provides benefits to many markets. Additionally, it has implications to oil resistance and repellency, oil slip resistance, and paint and coating options allowing more environmentally friendly options to be used.

Algae based foam compositions also exhibit tailorable properties with ratios of protein to mineral content being controllable which can vary foam properties to achieve the targeted performance characteristics. Compared to other renewable feedstock options these characteristics achieved through the diversity of algae available is unique and allows for more flexibility in foam product specifications. Additionally, given the positive environmental impacts of algae removal as well as the fast growth, and low impact of acquisition algae offers many environmental benefits over other renewable material options that exist in the market currently including but not limited to a route to carbon sequestration and its accepted use as a carbon credit generating commodity.

An example algae-based foam product includes 40% algae by weight and the balance is resin. Depending on the intended end use, the algae fraction can be modified. For example, if forming a flexible foam for use in footwear and shoe components, up to 30% algae can be incorporated with a desired thermoplastic resin. An algae-based thermoplastic foam may have a density that ranges from about 1 or 5 or 10 to 30 to about 100 or 200 or 300 to about 400 kg/m$^3$ or more.

Masterbatch can be defined as a solid additive for plastic used for imparting properties to plastics (additive masterbatch). Masterbatch is typically a concentrated mixture of additives encapsulated during a heat process into a carrier resin which is then cooled and cut into a granular shape. Masterbatch allows the processor to form polymer economically during the plastics manufacturing process. Masterbatch also allows for greater economies of scale in production since one masterbatch maybe used in multiple product compounds to achieve a wide range of product properties. In an example, a thermoplastic masterbatch may be made from an environmental mixed culture of microalgae having 39% protein and 28% ash wherein the thermoplastic masterbatch is suitable for the production of thermoplastic foam products. In another example, a thermoplastic masterbatch may be made from a freshwater macroalgae source such as Ulva with 20% protein and 31% ash blended with a cyanobacterial algae source, which is naturally very high in protein at around 68% protein and 8% ash at an equal ratio such that the final mixed algae composition is around about 44% protein and 20% ash. Since the final algae composition has a similar range of protein to ash ratios and both sources contain very little carbohydrate, the masterbatches were found to be capable of being used interchangeably and were both capable of producing the same outcome in a foam product.

In a further example, a thermoplastic foam product produced with algae and a thermoplastic elastomer such as EVA generates a foam with properties suitable for footwear products with densities ranging from 0.05 g/cm$^3$ to 0.9 g/cm$^3$, a hardness from 10 to 80 Asker C, a compression set from 30% to 80%, a rebound from 20% to 70%, a Din Abrasion from 400 to 100 mm, a tear strength from 1 to 20 kg/cm, and an algae content from 1 to 35% algae.

In yet another example, a thermoplastic injection molded product produced with algae and a thermoplastic elastomer such as SBS or SEBS generates an injection molded good with properties suitable for footwear products with densities from 0.1 g/cm$^3$ to 1.3 g/cm$^3$, a hardness from 75 to 35 shore A, a Din Abrasion from 300 to 80 mm, tear strength from 5 to 50 kg/cm, and an algae content from 1 to 40% algae.

In still yet another example, thermoplastic foam product produced with algae and a thermoplastic elastomer with olefin chemistry (TPO) generates a foam with properties suitable for footwear products having a density from 0.05 g/cm$^3$ to 0.9 g/cm$^3$, a hardness from 10 to 80 Asker C, a compression set from 30% to 80%, a rebound from 20% to 70%, a Din Abrasion from 400 to 100 mm, a tear strength from 1 to 20 kg/cm, and an algae content from 1 to 35% algae.

In yet another form, a thermoplastic film product produced with algae and a thermoplastic elastomer and biodegradable polymer polybutylene adipate-co-terephthalate (PBAT) generates a thermoplastic film with properties suitable for agricultural purposes with a thickness from 0.1 to 10 mil, a tear strength from 100 to 10,000 gf, a tensile strength at break from 500 to 100,000 psi and an algae content from 1 to 20% algae.

In still yet another form, a thermoplastic product is produced with algae where a biodegradable base resin is used. Wherein the degradation of the algae polymer composite was found to enhance plant growth with around about a 300% improvement in above ground plant foliage production. In a further example, the biodegradable base resin was capable of passing an ASTM D6400 industrial testing protocol in 9 months, but when used in the algae based composite the new algae based material biodegraded in industrial composting conditions in 4 to 5 months and was found to even take on marine biodegradability characteristics degrading in marine field tests in under a year. The enhanced biodegradability and plant growth stimulation is expected to be imparted by the incorporation of algae biomass into the masterbatch and is specifically enhanced by the nutritive contributions of the protein-rich algae meal. Protein-rich algae meal can be found to provide an excellent source of nitrogen and is often found to contain potassium and/or phosphorus sources in excess of 1% of the biomass by weight. The nitrogen, phosphorus, and potassium sources are generally found as organic compounds stored in the biomass which are encased in biodegradable polymer. The release of nutrients is therefore dependent on the polymeric materials biodegradation rate and is found to be slow release preventing over fertilization and fertilizer burns to plant roots which negatively impact plant health.

It should be noted that the steps described in the method of use can be carried out in many different orders according to user preference. The use of "step of" should not be interpreted as "step for", in the claims herein and is not intended to invoke the provisions of 35 U.S.C. § 112 (f). Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the disclosure described herein are exemplary and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. An algae-based thermoplastic composition comprising:
   (a) a protein-rich algae biomass selected from either microalgae, macroalgae or combinations thereof, wherein the protein content is greater than or equal to 15% by weight of the algae biomass and the algae biomass is dried to a moisture content of less than or equal to 15% by weight and having a particle d99 of up to 200 microns, wherein the dried algae biomass is at least 5% by weight of the thermoplastic composition;
   (b) a resin configured to exhibit rheological properties suitable for blending with algae including a melting temperature less than 250° C. and a melt flow rate in excess of 0.01 g/10 min.

2. The thermoplastic composition of claim 1, wherein the algae biomass is provided having a protein content of greater than 20% by weight.

3. The thermoplastic composition of claim 1, wherein the algae biomass comprises a member from the group consisting of cyanobacteria and a Cyanophyta, Charophyta, Chlorophyta, Phaeophyta, Chrysophyta, Bacillariophyta, Haptophyta, and Rhodophyta phylum microalgae.

4. The thermoplastic composition of claim 1, wherein the algae biomass is sourced from a plurality of algae sources including a mineral rich algae selected from the group consisting of diatoms, coccalithophores, coralline and combinations thereof.

5. The thermoplastic composition of claim 1, wherein the algae biomass comprises a dry weight of 15 to 90% protein, 5 to 50% carbohydrates, and 5 to 80% mineral and/or inorganic ash content.

6. The thermoplastic composition of claim 1, wherein the algae biomass comprises a dry weight of 20 to 85% protein, 10% to 45% carbohydrate, and 10 to 75% mineral and/or inorganic ash content.

7. The thermoplastic composition of claim 1, wherein the algae biomass comprises a dry weight of 25 to 80% protein, 15% to 40% carbohydrate, and 15 to 70% mineral and/or inorganic ash content.

8. The thermoplastic composition of claim 1, wherein the algae biomass comprises a dry weight of 35-50% protein, 5-30% carbohydrate and 25-40% mineral and/or inorganic ash content.

9. The thermoplastic composition of claim 1, wherein the algae biomass is provided as a powder milled to an average particle size between 1 and 80 micron.

10. The thermoplastic composition of claim 1, further comprising a compatibilizer configured to increase compatibility between the algae and the resin, wherein the compatibilizer includes functionalization selected from the group consisting of side chain modified polymers, block copolymers, grafted compatibilizer, reactive compatibilizers with glycidyl methacrylate, butyl acrylate, maleic anhydride groups or coupling agents selected from the group consisting of peroxides, isocyanates, and glyoxal.

11. The thermoplastic composition of claim 1, wherein the resin further comprises a member selected from the group consisting of synthetic, plant-based, bio-based, renewably-sourced, petroleum sourced resins and combinations thereof.

12. The thermoplastic composition of claim 1, wherein the resin is selected from the group consisting of polyesters, polyethylene terephthalate (PET), polybutylene terephthalate (PBT), polyethylene terephthalate glycol (PETG), polytrimethylene terephthalate (PTT), polycarbonate, biodegradable resins, polylactic acid (PLA), polybutylene succinate (PBS), polybutylene adipate-co-terephthalate (PBAT), polyhydroxyalkanoates (PHA), polyolefins such as polyethylene (PE), polypropylene (PP), polybutene (PB), polyisobutylene (PI B), thermoplastic elastomers such as thermoplastic polyurethanes (TPU), ethylene vinyl acetate (EVA), thermoplastic polyolefin elastomers (TPO), thermoplastic vulcanizates (TPV), thermoplastic copolyesters (TPE-E), thermoplastic polyamides (TPA), thermoplastic styrenic block copolymers (TPS), thermoplastic ester-ether copolymers (TPC), thermoplastic amide-ether copolymers (TPE-A), polyacrylonitrile butadiene styrene (ABS), polyacrylonitrile styrene acrylate (ASA), polystyrene acrylonitrile (SAN), polystyrene butadiene (SB), polystyrene (PS) nylon, polyvinyl alcohol (PVA), polyvinylidene chloride (PVDC) and combinations thereof.

13. A thermoplastic composition of claim 1 wherein the thermoplastic composition is a foam and further comprises a foaming ingredient configured to produce a foam with a density from 1 to 400 kg/m3.

14. The thermoplastic composition of claim 13, wherein the foaming ingredient is one or more additives selected from the group consisting of crosslinkers, peroxide-based crosslinking agents, isocyanate-based crosslinking agents, sulfur-based crosslinking agents, aziridine-based crosslinking agents, dialdehyde-based crosslinking agents, compatibilizers, plasticizers, accelerants, catalysts, and combinations thereof.

15. The thermoplastic composition of claim 13, wherein the foaming ingredient includes a physical or chemical blowing agent.

16. A shoe component comprising a thermoplastic composition of claim 1, wherein the shoe component is selected from the group consisting of an insole, outsole, and midsole.

17. A method of forming a final product comprising an algae-based thermoplastic composition, the method comprising:
(a) grinding a protein-rich algae biomass into an algae powder having at least 15% protein content by weight;
(b) drying the algae powder to form a relatively dried algae biomass powder having a moisture content of less than 15% by weight;
(c) premixing and preheating a thermoplastic resin to a desired temperature and viscosity to form a molten thermoplastic;
(d) mixing the algae powder with the molten thermoplastic forming a thermoplastic-algae blend;
(e) optionally adding additives, plasticizers, compatibilizers and/or foaming agents;
(f) dispersing the thermoplastic-algae blend; and
(g) forming a predetermined final product using the algae-thermoplastic blend.

18. The method of claim 17, wherein the resin is selected from the group consisting of polyesters, polyolefins, thermoplastic elastomers, styrenics, polyamides, polyethers, polyvinyl chlorides (PVC), thermoplastic polyurethanes (TPU), polybutylene adipate-co-terephthalate (PBAT), polyethylene (PE), ethylene-vinyl acetate (EVA), copolymers, and combination thereof.

19. The method of claim 17, wherein the final product is a shoe component selected from the group consisting of an insole, outsole, and midsole.

20. The method of claim 17, further comprising an intermediate step of pelletizing the thermoplastic-algae blend to form a masterbatch prior to dispersing in final product composition.

* * * * *